United States Patent
Steinmann

Patent Number: 5,106,932
Date of Patent: Apr. 21, 1992

[54] BENZOATES CONTAINING A SUBSTITUENT HAVING OLEFINIC UNSATURATION

[75] Inventor: Alfred Steinmann, Praroman, Switzerland

[73] Assignee: Ciba-Geigy Corporation, Ardsley, N.Y.

[21] Appl. No.: 731,188

[22] Filed: Jul. 15, 1991

[30] Foreign Application Priority Data

Jul. 18, 1990 [CH] Switzerland .......... 2385/90

[51] Int. Cl.$^5$ .......... C08F 20/26; C08F 120/36
[52] U.S. Cl. .......... 526/320; 526/292.3; 560/104
[58] Field of Search .......... 526/320, 292.3; 560/104

[56] References Cited

U.S. PATENT DOCUMENTS

| | | | |
|---|---|---|---|
| 3,515,552 | 6/1970 | Smith | 430/281 |
| 3,645,970 | 2/1972 | Kleiner | 560/104 |
| 3,779,778 | 12/1973 | Smith et al. | 96/115 |
| 4,939,070 | 7/1990 | Brunsvold et al. | 430/312 |
| 4,965,316 | 10/1990 | Steinmann | 526/240 |

Primary Examiner—Paul R. Michl
Assistant Examiner—Tae H. Yoon
Attorney, Agent, or Firm—JoAnn Villamizar

[57] ABSTRACT

Polymers suitable for use as positive photoresists can be prepared, in the absence or presence of other olefinically unsaturated monomers, from benzoates comprising an olefinic unsaturated substituent and consisting of formula I

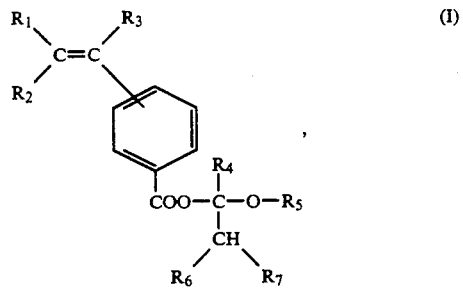

wherein $R_1$ and $R_2$ are each independently of the other a hydrogen atom, $C_1$–$C_4$alkyl or phenyl, $R_3$ is a hydrogen atom, methyl or a halogen atom, $R_4$ is a hydrogen atom or methyl, $R_5$ is $C_1$–$C_4$alkyl or $C_6$–$C_{12}$aryl, and $R_6$ and $R_7$ are each independently of the other a hydrogen atom, $C_1$–$C_4$alkyl or $C_6$–$C_{12}$aryl, and $R_5$ and $R_7$, when taken together, may also be an unsubstituted or a $C_1$–$C_4$alkyl-, $C_1$–$C_4$alkoxy-, $C_6$–$C_{12}$aryl- or $C_6$–$C_{12}$aryloxy-substituted ethylene, propylene or butylene radical.

5 Claims, No Drawings

BENZOATES CONTAINING A SUBSTITUENT HAVING OLEFINIC UNSATURATION

The present invention relates to novel benzoates which comprise a substituent having olefinic unsaturation, to polymers prepared with said benzoates, to positive-acting, radiation-sensitive compositions containing said novel polymers, and to a substance which forms an acid upon exposure to actinic radiation.

Positive-working, radiation-sensitive compositions and the use thereof as photoresists are known in the art. In addition to high sensitivity in the UV range, such photoresists must be easy to develop and have good resistance to etching.

Positive-working photoresist compositions comprising a water-soluble organic compound having specific acid-degradable linkages and a compound which forms acid upon exposure to actinic radiation are disclosed, for example, in U.S. Pat. No. 3,779,778. These photoresist compositions can only be developed in quite strongly alkaline solutions and they have poor heat stability.

The positive-working photoresist composition disclosed in EP-A-0 254 853 give, after exposure and development, images of high heat stability, but their light-sensitivity is relatively poor and they can only be developed in strongly alkaline aqueous solutions.

It has now been found that polymers prepared from benzoates comprising a substituent having olefinic unsaturation can be used with advantage for radiation-sensitive, positive-working compositions. The photoresists obtained therefrom have enhanced sensitivity to actinic radiation, and can be developed after exposure under very mild development conditions, for example in a very weakly alkaline medium, such as 1% by weight aqueous $NaHCO_3$ solution. Layers with submicron resolution can be prepared, so that the photoresists can also be used for making semiconductors. Furthermore, the structures obtained from the photoresists of this invention have excellent heat stability.

Specifically, the invention relates to benzoates comprising an olefinic unsaturated substituent and consisting of formula I

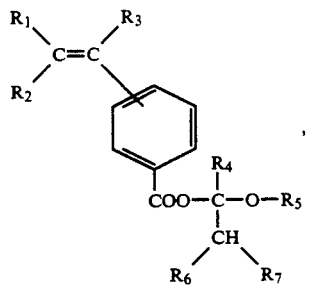

wherein $R_1$ and $R_2$ are each independently of the other a hydrogen atom, $C_1-C_4$alkyl or phenyl, $R_3$ is a hydrogen atom, methyl or halogen atom, $R_4$ is a hydrogen atom or methyl, $R_5$ is $C_1-C_4$alkyl or $C_6-C_{12}$aryl, and $R_6$ and $R_7$ are each independently of the other a hydrogen atom, $C_1-C_4$alkyl or $C_6-C_{12}$aryl, and $R_5$ and $R_7$, when taken together, may also be an unsubstituted or a $C_1-C_4$alkyl-, $C_1-C_4$alkoxy-, $C_6-C_{12}$aryl- or $C_6-C_{12}$aryloxy-substituted ethylene, propylene or butylene radical.

In formula I, $R_1$ and $R_2$ are preferably each independently of the other a hydrogen atom or $C_1-C_4$alkyl, $R_3$ is a hydrogen atom or methyl, and the olefinically unsaturated group at the ring is in para-position to the carbonyloxy group, $R_4$ is a hydrogen atom or methyl, $R_5$ is $C_1-C_4$alkyl and $R_6$ and each independently of the other a hydrogen atom or $C_1-C_4$alkyl, and $R_5$ and $R_7$, when taken together, may also be an unsubstituted or a $C_1-C_4$alkyl-, $C_1-C_4$alkoxy- or phenoxy-substituted ethylene, propylene or butylene radical.

More particularly, in formula I $R_1$, $R_2$, $R_3$ and $R_4$ are each independently of one another a hydrogen atom or methyl, and the olefinically unsaturated group at the ring is in para-position to the carbonyloxy group, $R_5$ is methyl and $R_6$ and $R_7$ are each independently of the other a hydrogen atom or methyl, and $R_5$ and $R_7$, when taken together, may also be an unsubstituted or a methyl-substituted ethylene or propylene radical.

An alkyl substituent $R_1$, $R_2$, $R_5$, $R_6$ or $R_7$ may be branched or, preferably, straight-chain, and is typically methyl, ethyl, n-propyl, isopropyl and n-butyl.

$R_3$ as halogen is preferably chloro or bromo.

$C_6-C_{12}$Aryl is phenyl, biphenyl or naphthyl, each unsubstituted or carrying one or more substituents. Suitable substituents may be halogen atoms, preferably chlorine or bromine atoms, or nitro groups. Suitable substituted aryl groups are typically o-chlorophenyl, o-nitrophenyl, 2,4-dichlorophenyl and 2-chloronaphthyl.

$C_1-C_4$Alkoxy substituents may suitably be methoxy, ethoxy or n-propoxy, and $C_6-C_{12}$aryloxy substituents may be phenoxy and naphthoxy.

Particularly preferred compounds of formula I are the tetrahydropyran-2-yl and tetrahydrofuran-2-yl ester of 4-vinylbenzoic acid.

The compounds of formula I may be prepared by reacting a compound of formula II

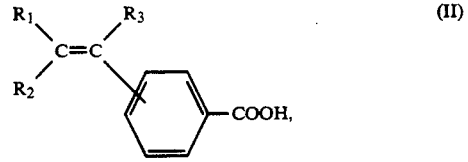

wherein $R_1$, $R_2$ and $R_3$ have the same meanings as in formula I, with a compound of formula III

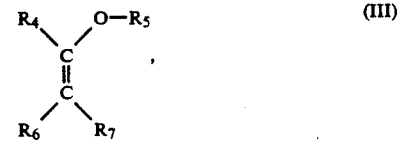

wherein $R_4$, $R_5$, $R_6$ and $R_7$ have the same meanings as in formula I, in an acid medium, to a compound of formula I.

The compounds of formula II are known, for example from DE patent 3,641,099, and some are commercially available. Representative examples of compounds of formula II are 4- or 2-vinylbenzoic acid, 4-(1'-chloro)-vinylbenzoic acid, 4-isopropenylbenzoic acid and 4-isobutenylbenzoic acid The compounds of formula III are also known compounds, some of which are commercially available. Where in formula III $R_5$, $R_6$ and $R_7$ are each independently of one another $C_1$–$C_4$alkyl or $C_6$–$C_{12}$aryl, these compounds may be methylisobutenyl ether, phenylisobutenyl ether, methylstyryl ether, methylvinyl ether or ethylvinyl ether.

Where $R_5$ and $R_7$ together in formula III are an alkylene radical, the compounds may be 2,3-dihydropyran, 2,3-dihydrofuran or 2,3,4,5-tetrahydrooxepine.

Where $R_5$ and $R_7$ together in formula III are an alkoxy-substituted alkylene radical, the compounds may be 2-methoxy-3,4-dihydropyran, which is commercially available (ex Fluka Chemie).

The acid medium of the reaction solution may be prepared by adding to the reaction solution a few drops of concentrated hydrochloric acid or sulfuric acid.

The reaction of the compounds of formula II with the compounds of formula III is preferably carried out in an inert gas atmosphere, more particularly under nitrogen, and at slightly elevated temperature in the range from ca. 25°–80° C. As mentioned at the outset, the compounds of formula I are useful monomers which, when polymerised, in the absence or presence of comonomers having olefinic unsaturation, may be used as radiation-sensitive and heat-stable resist material.

The present invention thus also relates to polymers having a molecular weight (Mw) of $10^3$ to $10^6$, measured by gel permeation chromatography, and containing, based on the total amount of structural units present in the polymer, 100 to 5 mol % of structural repeating units of formula IV

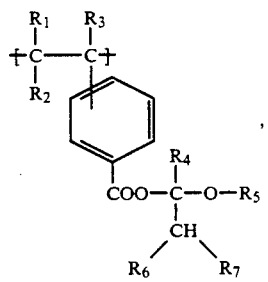

(IV)

and 95 to 0 mol % of the structural repeating unit of formula V

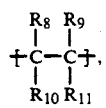

(V)

wherein $R_1$, $R_2$, $R_3$, $R_4$, $R_5$, $R_6$ and $R_7$ are as defined for formula I, $R_8$ and $R_9$ are each independently of the other a hydrogen atom, unsubstituted $C_1$–$C_4$alkyl or $C_1$–$C_4$alkyl which is substituted by halogen atoms, cyano or nitro groups, or is unsubstituted phenyl or naphthyl or phenyl or naphthyl which are each substituted by halogen atoms or $C_1$–$C_4$alkoxy, hydroxy, cyano or nitro groups, and $R_{10}$ and $R_{11}$ are each independently of the other a hydrogen or halogen atom, unsubstituted $C_1$–$C_{12}$alkyl or $C_1$–$C_{12}$alkyl which is substituted by halogen atoms, cyano or nitro groups, unsubstituted phenyl, naphthyl or benzyl, or phenyl, naphthyl or benzyl which are substituted each by halogen atoms, hydroxy, cyano or nitro groups, or by $C_1$–$C_4$alkyl or $C_1$–$C_4$alkoxy, or are a radical selected from the group consisting of —$OR_{12}$, —$COOR_{13}$ and —$COR_{14}$, where $R_{12}$ and $R_{13}$ are each independently of the other a hydrogen atom, unsubstituted $C_1$–$C_{12}$alkyl or $C_1$–$C_{12}$alkyl which is substituted by halogen atoms, cyano or nitro groups, unsubstituted phenyl or naphthyl, or phenyl or naphthyl which are each substituted by halogen atoms, cyano or nitro groups, $C_1$–$C_4$alkyl or $C_1$–$C_4$alkoxy, and $R_{14}$ has the same meaning as $R_{12}$ and is also the radical

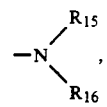

wherein $R_{15}$ and $R_{16}$ have each independently of the other the same meaning as $R_{12}$, or wherein $R_{10}$ and $R_{11}$, when taken together, are the radical

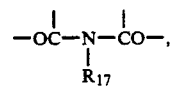

wherein $R_{17}$ is a hydrogen atom or unsubstituted or hydroxy-substituted phenyl.

The polymers of this invention preferably have a molecular weight (Mw) of 5000 to 500 000, most preferably of 20 000 to 150 000.

The polymers of this invention further preferably contain 100 to 20 mol %, most preferably 100 to 50 mol %, of structural repeating units of formula IV and 80 to 0 mol %, most preferably 50 to 0 mol %, of the structural repeating unit of formula V.

In the structural repeating unit of formula IV, $R_1$, $R_2$, $R_3$, $R_4$, $R_5$, $R_6$ and $R_7$ have the same preferred meaning as in formula I.

$R_8$, $R_9$, $R_{10}$ and $R_{11}$ as alkyl in the structural repeating unit of formula V is straight-or branched-chain, preferably straight-chain, alkyl.

Halogen substituents may be fluorine, chlorine, bromine or iodine atoms, and are preferably chlorine or bromine atoms.

Unsubstituted or substituted alkyl may be methyl, ethyl, 2-chloroethyl, 2-nitroethyl, n-propyl, isopropyl, n-butyl, sec-butyl, tert-butyl, n-pentyl, isoamyl, n-hexyl, 2-ethylhexyl, n-decyl, 6-nitrohexyl or 9-bromononyl.

Substituted phenyl or naphthyl is typically o-, m- or p-chlorophenyl, o-, m- or p-tolyl, xylyl, 2-nitrophenyl or α-chloronaphthyl.

In the structural repeating unit of formula V, $R_8$, $R_9$ and $R_{10}$ are preferably each independently of one another a hydrogen atom, $C_1$–$C_6$alkyl or phenyl, and $R_{11}$ is preferably a halogen atom, phenyl or benzyl or a radical selected from the group consisting of —$OR_{12}$, —$COOR_{13}$ and —$COR_{14}$, wherein $R_{12}$, $R_{13}$ and $R_{14}$ are each independently of one another a hydrogen atom, $C_1$–$C_6$alkyl or phenyl, and $R_{14}$ is also the radical

wherein $R_{16}$ and $R_{17}$ each independently of the other has the preferred meaning of $R_{12}$.

The polymers of this invention can be prepared by subjecting compounds of formula I or mixtures of compounds of formula I and compounds of formula V a present therein in an amount of up to 95 mol %, preferably of up to 80 mol %, most preferably of up to 50 mol %,

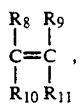
(Va)

wherein $R_8$, $R_9$, $R_{10}$ and $R_{11}$ are as defined for formula V, to radical polymerisation in known manner.

The radical polymerisation can be carried out by different techniques, for example those described by S. Sandler and W. Karo in "Polymer Synthesis" Vol. 1–3, 1968, Academic Press, New York. Conventional polymerisation methods are typically mass polymerisation, or solvent, emulsion, suspension or precipitation polymerisation.

The compounds of formula V are known and some are commercially available. In addition to olefins, such as ethylene or propylene, the vinyl compounds may be mentioned as particular examples of compounds of formula V. Examples of such monomers are the styrene types, for example styrene, $\alpha$-methylstyrene, $p$-methylstyrene or $p$-hydroxyphenylstyrene, $\alpha,\beta$-unsaturated acids and esters or amides thereof, including acrylic acid, methyl acrylate, acrylamide, the corresponding methacrylic compounds, maleic acid, methyl maleate, maleimides or $p$-hydroxyphenylmaleimides, halogen-containing vinyl compounds, such as vinyl chloride, vinyl fluoride, vinylidene chloride or vinylidene fluoride, and vinyl esters, such as vinyl acetate or vinyl ethers, for example methyl vinyl ether or butyl vinyl ether.

Examples of further suitable compounds are the allyl compounds such as allyl chloride, allyl bromide or allyl cyanide.

The polymerisation is normally initiated by one of the conventional initiators of free-radical polymerisation. These include thermal initiators such as azo compounds, typically azoisobutyronitrile (AIBN), or peroxides such as benzoyl peroxides, or redox initiator systems, such as a mixture of iron(III) acetylacetonate, benzoin and benzoyl peroxide, or photochemical free-radical formers such as benzoin or benzil methylketal.

The polymerisation is preferably carried out in solution. The reaction temperature is normally in the range from 10° to 200° C., preferably from 40° to 150° C. and, most preferably, from 40° to 100° C.

Any solvents present must be inert under the reaction conditions. Suitable solvents include aromatic hydrocarbons, chlorinated hydrocarbons, ketones and ethers. Representative examples of such solvents are benzene, toluene, xylene, ethylbenzene, isopropylbenzene, ethylene chloride, propylene chloride, methylene chloride, chloroform, methyl ethyl ketone, acetone, cyclohexanone, diethyl ether or tetrahydrofuran. As mentioned at the outset, the polymers of this invention are useful materials for positive photoresists which have a very good high sensitivity to acids and, together with acid-generating photoinitiators, form a radiation-sensitive composition. The sensitivity of the novel polymers to acids persists even in high layer thicknesses, for example of 30 µm. In addition, the compounds obtained by acid cleavage from the novel polymers are soluble in bases. In contrast, the novel polymers are very stable to bases, so that very good differentiation between exposed and unexposed areas is obtained in the photoresist.

Accordingly, the invention also relates to a positive-working, radiation-sensitive composition which comprises, based on the total amount of components a) and b), a) 85 to 99% by weight of a polymer containing, based on the total amount of structural units present in the polymer, 100 to 5 mol % of the structural repeating unit of formula IV and 95 to 0 mol % of the structural repeating unit of formula V, and b) 1 to 15% by weight of a substance which forms an acid upon exposure to actinic radiation.

The radiation-sensitive composition will preferably contain 90 to 99% by weight, more particularly 95 to 98% by weight, of component a), and 1 to 10% by weight, more particularly 2 to 5% by weight, of component b), and component a) preferably contains 100 to 20 mol %, more particularly 100 to 50 mol %, of the structural repeating unit of formula IV, and 80 to 0 mol %, more particularly 50 to 0 mol %, of the structural repeating unit of formula V.

A large number of compounds are known as radiation-sensitive components b) which, upon exposure to light, form or eliminate an acid. These compounds include, for example, the diazonium salts used in the diazo process, the o-quinone-diazides used in known positive-working copying compositions, or also halogen compounds which form a hydrohalic acid upon irradiation. Compounds of this type are disclosed, for example, in U.S. Pat. Nos. 3,515,552, 3,536,489 or 3,779,778, and in DE-OS 2 718 259, 2 243 621 or 2 610 842.

Particularly suitable radiation-sensitive components b) of the compositions of this invention are photoinitiators selected from the group consisting of iodonium or sulfonium salts. Such compounds are described, for example, in "UV-Curing, Science and Technology" (Editor: S. P. Pappas, Technology Marketing Corp., 642 Westover Road, Stanford, Conn., USA).

Sulfoxonium salts can also be used as radiation-sensitive compounds. Such salts are disclosed, for example, in EP patent 35 969 or in EP-A 44 274 and 54 509. Particular mention is made of aliphatic sulfoxonium salts which absorb in the low UV range.

It is also possible to use those compounds which generate sulfonic acids when irradiated with actinic light. Such compounds are known per se and are described, for example, in GB-A 2 120 263, EP-A 84 515; 37 512 or 58 638 and in U.S. Pat. Nos. 4,258,121 or 4,371,605.

If salts are used as the radiation-sensitive, acid-releasing components b), then said salts are preferably soluble in organic solvents. Most preferably, these salts are products with complex acids, for example with hydrofluoroboric acid, hexafluorophosphonic acid, hexafluoroarsenic acid or hexafluoroantimonic acid.

Binders c) may also be added to the novel radiation-sensitive compositions. It is especially useful to add binders if the light-sensitive compositions are liquid or low viscosity mixtures. In this case, the novel polymer acts as conventional solution inhibitor. Upon exposure, a polymeric compound which is soluble in bases forms from the polymer by acid-catalysed hydrolysis.

The amount of binder c) can be 30–90% by weight, preferably 60–90% by weight, based on the total amount of components a), b) and c).

The choice of binder is made according to the field of use and the properties required therefor, such as the ability to develop in aqueous and aqueous alkaline solvent systems or adhesion to substrates.

Exemplary of suitable binders c) are novolaks which are derived from an aldehyde, preferably acetaldehyde or formaldehyde, but more particularly from formaldehyde, and a phenol. The phenolic component of this binder is preferably phenol itself or also halogenated phenol, for example substituted by one or two chlorine atoms, preferably p-chlorophenol, or it is a phenol which is substituted by one to two $C_1$–$C_9$alkyl groups, for example o-, m- or p-cresol, a xylenol, p-tert-butylphenol or p-nonylphenol. The phenol component of the preferred novolaks can, however, also be p-phenylphenol, resorcinol, bis(4-hydroxyphenyl)methane or 2.2-bis(4-hydroxyphenyl)propane.

Some of the phenolic hydroxyl groups of these novolaks may be modified by reaction with, for example, chloroacetic acid, isocyanates, epoxides or carboxylic anhydrides.

Further suitable binders are typically copolymers of maleic anhydride with styrene or vinyl ethers or 1-alkenes.

Examples of further suitable binders are copolymers of maleic anhydride with styrene or vinyl ethers or 1-alkenes. Further binders which can be used are: homopolymeric and copolymeric acrylates and methacrylates, for example copolymers of methyl methacrylate/ethyl acrylate/methacrylic acid, poly(alkyl methacrylates) or poly(alkyl acrylates), where alkyl=-$C_1$–$C_{20}$.

Preferably, the binder used is an alkali-soluble substance, for example a novolak (which may be modified as described above), a copolymer of maleic anhydride with styrene or vinyl ethers or 1-alkenes, as well as a copolymer of esters of acrylic acid or methacrylic acid with ethylenically unsaturated acids, such as methacrylic acid or acrylic acid.

Yet further auxiliary resins may be added to these alkali-soluble binders, as is customary in positive-working systems. These auxiliary resins are typically vinyl polymers such as polyvinyl acetate, polyacrylates, poly(alkylmethacrylates) or poly(alkylacrylates), in which alkyl is $C_1$–$C_{20}$alkyl, polyvinyl ethers or polyvinyl pyrrolidones. Generally, however, not more than 20% by weight, based on the amount of alkali-soluble binder, of these auxiliary resins is added.

The compositions of this invention may contain further conventional modifiers such as stabilisers, pigments, dyes, fillers, adhesion promoters, levelling agents, wetting agents and plasticisers. For application, the compositions may also be dissolved in suitable solvents.

The compositions of this invention have excellent suitability as coating agents for substrates of all kinds, for example wood, textiles, paper, ceramics, glass, plastics materials such as polyesters, polyethylene terephthalates, polyolefins or cellulose acetate, preferably in the form of films, and also of metals such as Al, Cu, Ni, Fe, Zn, Mg or Co, and of Si or $SiO_2$, on which it is desired to produce an image by image-wise exposure. The invention further relates to the coated substrates.

The preparation of the coated substrates can be effected, for example, by preparing a solution or suspension of the composition. The choice of solvent and the concentration depends mainly on the nature of the composition and on the coating method. The solution is uniformly applied to a substrate by known coating methods, for example by whirl coating, immersion, doctor coating, curtain coating, brushing, spraying and reverse roller coating. It is also possible to apply the light-sensitive layer to a temporary flexible support and then to coat the final substrate, for example a copper-clad circuit board, by coat transfer by means of lamination.

The add-on (layer thickness) and the nature of the substrate are contingent on the desired utility. A particular advantage of the compositions of the invention is that they can be used in widely varying layer thicknesses. This thickness range comprises values of ca. 0.5 $\mu$m to more than 100 $\mu$m. With conventional positive-working systems based on naphthoquinoneiazide, layer thicknesses greater than 10 $\mu$m can no longer be used.

Possible utilities of the compositions of this invention are as photoresists in the electronics field (galvanoresist, discharge resist, solvent resist), the production of printing plates such as offset plates or screen printing formes, mould etching, or as microresist in the production of integrated circuits.

The possible substrates and conditions for processing the coated substrates differ correspondingly.

Sheets made from polyester, cellulose acetate or plastics-coated papers are typically used for the photographic recording of information. Specially treated aluminium is used for offset formes, and copper-clad laminates are used for producing printed circuits, and silicon wafers are used for making integrated circuits. The layer thicknesses for photographic materials and offset printing formes are from ca. 0.5 $\mu$m to 10 $\mu$m, and for printed circuits 1 to ca. 100 $\mu$m.

After the substrate has been coated, the solvent is normally removed by drying to give a layer of photoresist on the substrate.

After image-wise exposure of the material in conventional manner, the exposed areas of the photoresist are washed out with a developer.

The choice of the developer depends on the type of photoresist, especially on the nature of the binder used or of the photolysis products. The developer may comprise aqueous solutions of bases to which organic solvents or mixtures thereof may be added.

Particularly preferred developers are the aqueous-alkaline solutions used for the development of naphthoquinone diazide/novolak resists. These include in particular aqueous solutions of alkali metal silicates, phosphates and hydroxides, or tetraalkylammonium compounds. These solutions may additionally contain minor amounts of wetting agents and/or organic solvents.

Typical organic solvents are those which are miscible with water and can be added to the developer liquids, for example 2-ethoxyethanol or acetone, as well as mixtures of two or more such solvents.

The expression "exposure to actinic radiation in a predetermined pattern" will be understood to mean exposure through a photomask which contains a predetermined pattern, for example a chromium mask or a photographic transparency, as well as exposure to a laser beam which is moved by logic control over the surface of the coated surface to produce an image.

The light-sensitivity of the compositions of this invention extends generally from the UV region (ca. 250 nm) to ca. 600 nm and is thus very wide ranging. Suitable light sources therefore comprise a large number of very widely varying types. Point light sources as well as arrays of reflector lamps are suitable. Examples are: carbon arcs, xenon arcs, mercury vapour lamps which may be doped with halogen atoms (metal halide lamps), fluorescent lamps, argon glow lamps, electronic flash lamps and photographic flood lamps. The distance between lamp and image material may vary substantially, depending on the utility and the type of lamp, for example from 2 cm to 150 cm. Particularly suitable light sources are laser light sources, for example argon ion lasers or crypton ion lasers. With this type of exposure, a photomask in contact with the photopolymer layer is no longer necessary, as the laser beam writes direct on to the layer. The high sensitivity of the compositions of the invention is very advantageous here and permits high writing speeds at relatively low intensities. This method can be used to make printed circuits for the electronics industry, lithographic offset plates or relief printing plates as well as photographic image recording materials.

The invention therefore relates also to the printing formes, printed circuits, integrated circuits or silver-free photographic films produced with the novel compositions.

EXAMPLE 1

Preparation of the tetrahydropyran-2-yl ester of 4-vinylbenzoic acid 20 g (135 mmol) of 4-vinylbenzoic acid and 22.7 g (270 mmol) of 3,4-dihydro-2H-pyran are charged to a 100 ml round flask equipped with magnetic stirrer. To the suspension are added 4 drops of concentrated hydrochloric acid, and the reaction mixture is stirred at 40° C. under nitrogen. After about 40 minutes, a clear solution is obtained. This solution is stirred for a further 40 minutes, then poured into ice-cold 2N sodium hydroxide solution. After two extractions with diethyl ether, the ether phase is washed with water and dried over sodium sulfate. The ether is removed on a rotary evaporator and the resultant liquid is dissolved in n-hexane. The solution is treated with activated carbon, filtered, and the solvent is removed on a rotary evaporator. The clear, colourless liquid is thereafter dried under a high vacuum.

Yield: 27.5 g (88% of theory). The substance cannot be distilled.

| Elemental analysis (microanalysis): | |
|---|---|
| calculated | found |
| C = 72.39% | 72.41% |
| H = 6.94% | 7.23% |

The $^1$H-NMR spectrum (CDCl$_3$) accords with the structure of the tetrahydropyran-2-yl ester of 4-vinylbenzoic acid.

EXAMPLE 2

Preparation of the tetrapyran-2-yl ester of 4-isopropenylbenzoic acid 5 g (31 mmol) of 4-isopropenylbenzoic acid and 5.2 g (62 mmol) of 3,4-dihydro-2H-pyran are are charged to a 25 ml round flask equipped with magnetic stirrer. To the suspension are added 2 drops of concentrated hydrochloric acid, and the reaction mixture is stirred at 40° C. under nitrogen. Over 20 minutes the suspension becomes a solution. After 60 minutes the solution is poured into ice-cold 2N sodium hydroxide solution. After extraction with 50 ml of ether, the organic phase is washed with water saturated with sodium chloride, dried over Na$_2$SO$_4$, filtered and concentrated by evaporation. The slightly brownish liquid is chromatographed over silica gel/chloroform. Yield: 2.7 g (36% of theory).

| Microanalysis: | |
|---|---|
| calculated | found |
| C = 73.15% | 73.20% |
| H = 7.37% | 7.59% |

The $^1$H-NMR spectrum (CDCl$_3$) accords with the structure of the tetrahydropyran-2-yl ester of 4-isopropenylbenzoic acid.

EXAMPLE 3

Preparation of the tetrafuran-2-yl ester of 4-vinylbenzoic acid 24 g (162 mmol) of 4-vinylbenzoic acid and 28.4 g (405 mmol) of 2,3-dihydrofuran are are charged to a 100 ml round flask equipped with magnetic stirrer. To the suspension are added 3 drops of concentrated hydrochloric acid, and the reaction mixture is stirred at 40° C. under nitrogen. Over 1 minute the suspension becomes a solution. After 30 minutes the solution is poured into ice-cold 1N sodium hydroxide solution. After two extractions with diethyl ether, the combined ether phase is washed with water, dried over sodium sulfate, and the ether is removed on a rotary evaporator. The clear liquid obtained boils at 150° C./0.03 mbar.

Yield: 28.6 g (81% of theory).

| Microanalysis: | |
|---|---|
| calculated | found |
| C = 71.54% | 71.51% |
| H = 6.47% | 6.60% |

The $^1$H-NMR spectrum (CDCl$_3$) accords with the structure of the tetrahydrofuran-2-yl ester of 4-vinylbenzoic acid.

EXAMPLE 4

Preparation of the 1-methoxyisobutyl ester of 4-vinylbenzoic acid

1-Methoxyisobutene is prepared according to the method described by H. Böhme and H. Bentler, in Chem. Ber. 1959, 89, 1464–1468, to give a liquid which is distilled under normal pressure over a packed column and which has a boiling point of 70° C. Analysis by gas chromatography shows the product to have a purity of 98%. The yield is 30%.

| Microanalysis: | |
|---|---|
| calculated | found |
| C = 69.7% | 68.6% |
| H = 11.7% | 11.2% |

The $^1$H-NMR spectrum (CDCl$_3$) accords with the structure of 1-methoxyisobutene.

15 g (100 mmol) of 4-vinylbenzoic acid are suspended in 17.2 g (200 mmol) of 1-methoxyisobutene. To this suspension are added 5 drops of concentrated hydrochloric acid and the reaction mixture is stirred for 7 hours at 40° C. The clear solution obtained is diluted with diethyl ether and extracted twice with aqueous NaHCO$_3$. The ether phase is dried over Na$_2$SO$_4$, then filtered and concentrated by evaporation. The residue is distilled at 125° C. and 0.065 mbar, giving 6 g of the 1-methoxyisobutyl ester of 4-vinylbenzoic acid in the form of a clear liquid.

| Microanalysis: | |
|---|---|
| calculated | found |
| C = 71.7% | 71.1% |
| H = 7.7% | 7.9% |

The $^1$H-NMR spectrum (CDCl$_3$) accords with the structure of the 1-methoxyisobutyl ester of 4-vinylbenzoic acid.

EXAMPLE 5

Preparation of the tetrahydropyran-2-yl ester of poly(4-vinylbenzoic acid)

8 g (34 mmol) of the tetrahydropyran-2-yl ester of 4-vinylbenzoic acid, 57 mg (1 mol %) of azoisobutyronitrile (AIBN) and 32 ml of toluene are charged to a 50 ml ampoule equipped with magnetic stirrer. The solution is degassed twice at −78° C., the ampoule is fused under a high vacuum, and polymerisation is carried out for 12 hours at 70° C. The viscous solution is poured into methanol, whereupon the polymer precipitates. The polymer is isolated, dried, and dissolved in 60 ml of methylene chloride. This solution is added dropwise to 800 ml of methanol and the precipitated polymer is isolated. The white polymer is dried at 40° C. under a high vacuum.

Yield: 5.8 g (72% of theory).

Molecular weight determination by gel permeation chromatography (GPC) in tetrahydrofuran (THF): Mw: 63 000 Mn: 34 000 Mw/Mn=1.85.

| Microanalysis: | |
|---|---|
| calculated | found |
| C = 72.39% | 72.24% |
| H = 6.94% | 7.10% |

EXAMPLE 6

Homopolymerisation of the tetrahydrofuran-2-yl ester of 4-vinylbenzoic acid 10 g (46 mmol) of the tetrahydrofuran-2-yl ester of 4-vinylbenzoic acid, 75 mg (1 mol %) of AIBN and 43 ml of toluene are charged to a 100 ml round flask equipped with magnetic stirrer. The solution is degassed twice at −78° C. and blanketed with argon. Polymerisation is carried out for 16 hours at 70° C. The viscous liquid is added dropwise to n-hexane, whereupon a white polymer precipitates. The polymer is isolated, dried, and dissolved in 100 ml of methylene chloride. This solution is added dropwise to 1.3 liters of n-hexane and the polymer is isolated and dried at 0.03 mbar/40° C.

Yield: 4.6 g (46% of theory).

GPC (THF): Mw: 37 000 Mn: 11 000 Mw/Mn=3.36.

| Microanalysis: | |
|---|---|
| calculated | found |
| C = 71.54% | 71.24% |

| -continued | |
|---|---|
| Microanalysis: | |
| calculated | found |
| H = 6.47% | 6.52% |

APPLICATION EXAMPLES

Example A 4 g of the tetrahydropyran-2-yl ester of poly(4-vinylbenzoic acid) and 0.2 g of thiophenoxyphenyldiphenylsulfonium hexafluoroarsenate are dissolved in 40 g of cyclopentanone. This solution is filtered through a 0.5 micron filter and applied to a silicon wafer. A homogeneous film is produced on the silicon wafer by whirl coating at 2500 rpm. The film is dried for 2 minutes at 90° C. The film thickness is 1.2 microns. The film is exposed through a mask and a narrow band filter with light of 308 nm wavelength. The exposure energy required is 4–5 mJ/cm$^2$. After exposure, the resist film is heated on a hot plate for 1 minute at 110° C. and then developed for 2 minutes at 22° C. The exposed zones are washed out in this development, so that the resist is positive. The resist film is rinsed with deionised water and dried at 90° C. Analysis by scanning electron microscopy shows that the resist resolves 0.5 micron structures and that the structures have an edge steepness of almost 90°.

Example B 4 g of the tetrahydrofuran-2-yl ester of poly(4-vinylbenzoic acid) and 0.2 g of thiophenoxyphenyldiphenylsulfonium hexafluoroarsenate are dissolved in 20 g of cyclopentanone. This solution is filtered through a 0.5 micron filter and applied to a silicon wafer. A homogeneous film is produced on the silicon wafer by whirl coating at 2500 rpm. The film is dried for 2 minutes at 90° C. The film thickness is 1 micron. The film is exposed and developed as in Example A. An exposure energy of 4 mJ/cm$^2$ at 308 nm suffices to resolve submicron structures.

What is claimed is:

1. A polymer having a molecular weight (Mw) of $10^3$ to $10^6$, measured by gel permeation chromatography, and containing, based on the total amount of structural units present in the polymer, 100 to 5 mol % of structural repeating units of formula IV

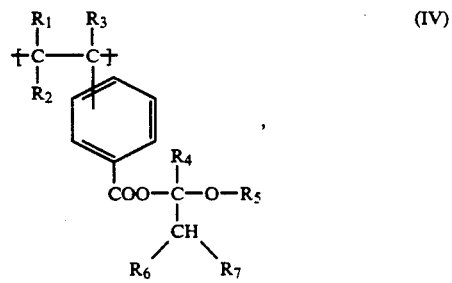

and 95 to 0 mol % of the structural repeating unit of formula V

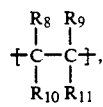

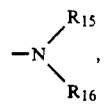

wherein $R_1$, $R_2$, $R_3$, $R_4$, $R_5$, $R_6$ and $R_7$ are as defined for formula I, $R_8$ and $R_9$ are each independently of the other a hydrogen atom, unsubstituted $C_1$-$C_4$alkyl or $C_1$-$C_4$alkyl which is substituted by halogen atoms, cyano or nitro groups, or is unsubstituted phenyl or naphthyl or phenyl or naphthyl which are each substituted by halogen atoms or $C_1$-$C_4$alkoxy, hydroxy, cyano or nitro groups, and $R_{10}$ and $R_{11}$ are each independently of the other a hydrogen or halogen atom, unsubstituted $C_1$-$C_{12}$alkyl or $C_1$-$C_{12}$alkyl which is substituted by halogen atoms, cyano or nitro groups, unsubstituted phenyl, naphthyl or benzy, or phenyl, naphthyl or benzyl which are substituted each by halogen atoms, hydroxy, cyano or nitro groups, or by $C_1$-$C_4$alkyl or $C_1$-$C_4$alkoxy, or are a radical selected from the group consisting of $-OR_{12}$, $-COOR_{13}$ and $-COR_{14}$, where $R_{12}$ and $R_{13}$ are each independently of the other a hydrogen atom, unsubstituted $C_1$-$C_{12}$alkyl or $C_1$-$C_{12}$alkyl which is substituted by halogen atoms, cyano or nitro groups, unsubstituted phenyl or naphthyl, or phenyl or naphthyl which are each substituted by halogen atoms, cyano or nitro groups, $C_1$-$C_4$alkyl or $C_1$-$C_4$alkoxy, and $R_{14}$ has the same meaning as $R_{12}$ and is also the radical wherein $R_{15}$ and $R_{16}$ have each independently of the other the same meaning as $R_{12}$.

2. A polymer according to claim 1, containing 100 to 20 mol % of the structural repeating unit of formula IV and 80 to 0 mol % of the structural repeating unit of formula V.

3. A positive-working, radiation-sensitive composition which comprises, based on the total amount of components a) and b),
   a) 85 to 99% by weight of a polymer according to claim 1 containing, based on the total amount of structural units present in the polymer, 100 to 5 mol % of the structural repeating unit of formula IV and 95 to 0 mol % of the structural repeating unit of formula V, and
   b) 1 to 15% by weight of a substance which forms an acid upon exposure to actinic radiation.

4. A composition according to claim 3, comprising
   a) 90 to 99% by weight of a polymer containing 100 to 20 mol % of the structural repeating unit of formula IV and 80 to 0 mol % of the structural repeating unit of formula V, and
   b) 1 to 10% by weight of a substance which forms an acid upon exposure to actinic radiation.

5. The printing formes, printed circuits, integrated circuits or silver-free photographic films produced with the composition as claimed in claim 3.

* * * * *